United States Patent
Buisson

(10) Patent No.: US 6,463,928 B1
(45) Date of Patent: Oct. 15, 2002

(54) PEDIATRIC PREPATORY AND INDUCTION ANESTHESIA DEVICE

(76) Inventor: Michael Irwin Buisson, 206 Willow Oaks Dr., Clinton, MS (US) 39056

( * ) Notice: Subject to any disclaimer, the term of this patent is extended or adjusted under 35 U.S.C. 154(b) by 0 days.

(21) Appl. No.: 09/286,952

(22) Filed: Apr. 6, 1999

(51) Int. Cl.$^7$ .............................................. A61M 16/00
(52) U.S. Cl. .......................... 128/203.12; 128/203.28; 128/204.28; 128/205.14
(58) Field of Search ....................... 128/200.24, 203.12, 128/203.22, 203.28, 203.29, 204.18, 204.26, 204.28, 204.29, 205.14, 205.15

(56) References Cited

U.S. PATENT DOCUMENTS

| | | | |
|---|---|---|---|
| 649,717 A | * 5/1900 | Browne | |
| 782,108 A | * 2/1905 | Coburn | |
| 1,567,868 A | * 12/1925 | Schroder | |
| 1,693,730 A | * 12/1928 | Schroder | |
| 2,020,643 A | * 11/1935 | Henion | 128/203 |
| 2,119,446 A | * 5/1938 | Sholes | 128/203 |
| 2,591,120 A | * 4/1952 | Blease | 128/29 |
| 3,747,600 A | * 7/1973 | Anderson | 128/188 |
| 3,960,148 A | * 6/1976 | Dryden | 128/188 |
| 4,109,651 A | * 8/1978 | Steigerwald | 128/145.8 |
| 4,250,876 A | * 2/1981 | Kranz | 128/202.22 |
| 4,596,246 A | * 6/1986 | Lyall | 128/202.22 |
| 4,653,493 A | * 3/1987 | Hoppough | 128/202.22 |
| 4,676,239 A | * 6/1987 | Humphrey | 128/205.17 |
| 4,938,210 A | * 7/1990 | Shene | 128/203.12 |
| 5,109,838 A | * 5/1992 | Elam | 128/203.12 |
| 5,121,746 A | * 6/1992 | Sikora | 128/203.12 |
| 5,222,491 A | * 6/1993 | Thomas | 128/205.13 |
| 5,284,160 A | * 2/1994 | Dryden | 128/203.12 |
| 5,285,775 A | * 2/1994 | Mayer | 128/205.13 |
| 5,400,779 A | * 3/1995 | De Resende | 128/205.24 |
| 5,404,873 A | * 4/1995 | Leagre et al. | 128/204.18 |
| 5,653,223 A | * 8/1997 | Pruitt | 128/200.21 |
| 5,690,096 A | * 11/1997 | Burch | 128/204.18 |
| 5,697,363 A | * 12/1997 | Hart | 128/201.24 |
| 5,778,872 A | * 7/1998 | Fukunaga et al. | 128/202.27 |
| 5,906,203 A | * 5/1999 | Klockseth et al. | 128/205.24 |

* cited by examiner

Primary Examiner—Aaron J. Lewis
Assistant Examiner—Mital Patel
(74) Attorney, Agent, or Firm—Phelps Dunbar, L.L.P.

(57) ABSTRACT

The Pediatric Prepatory and Induction Anesthesia Device ("PPIAD") is designed to aid anesthetists in effectively administering anesthetic gas to young patients. The PPIAD has a toy-like appearance, which calms the fears of children. The PPIAD also incorporates toy-like devices such as whistles and balloons. When the PPIAD is given to children prior to treatment, the child can play with it as a toy. During this play time, the PPIAD actually teaches the child proper breathing for the administration of anesthetic gas because the whistle and balloon are only activated by deep breathing. Thus, when the child is administered anesthetic gas with the PPIAD, the application of anesthetic gas is much more effective. In addition, as the anesthetic gas is applied with the PPIAD, the child is encouraged to breathe deeply to activate the toy-like devices, enhancing the application of anesthetic gas to the child. Thus, the PPIAD helps doctors provide effective care for child patients as it clams the fears of child patients during these medical procedures.

5 Claims, 1 Drawing Sheet

PEDIATRIC PREPATORY AND INDUCTION ANESTHESIA DEVICE

BACKGROUND OF THE INVENTION

Figure 1:
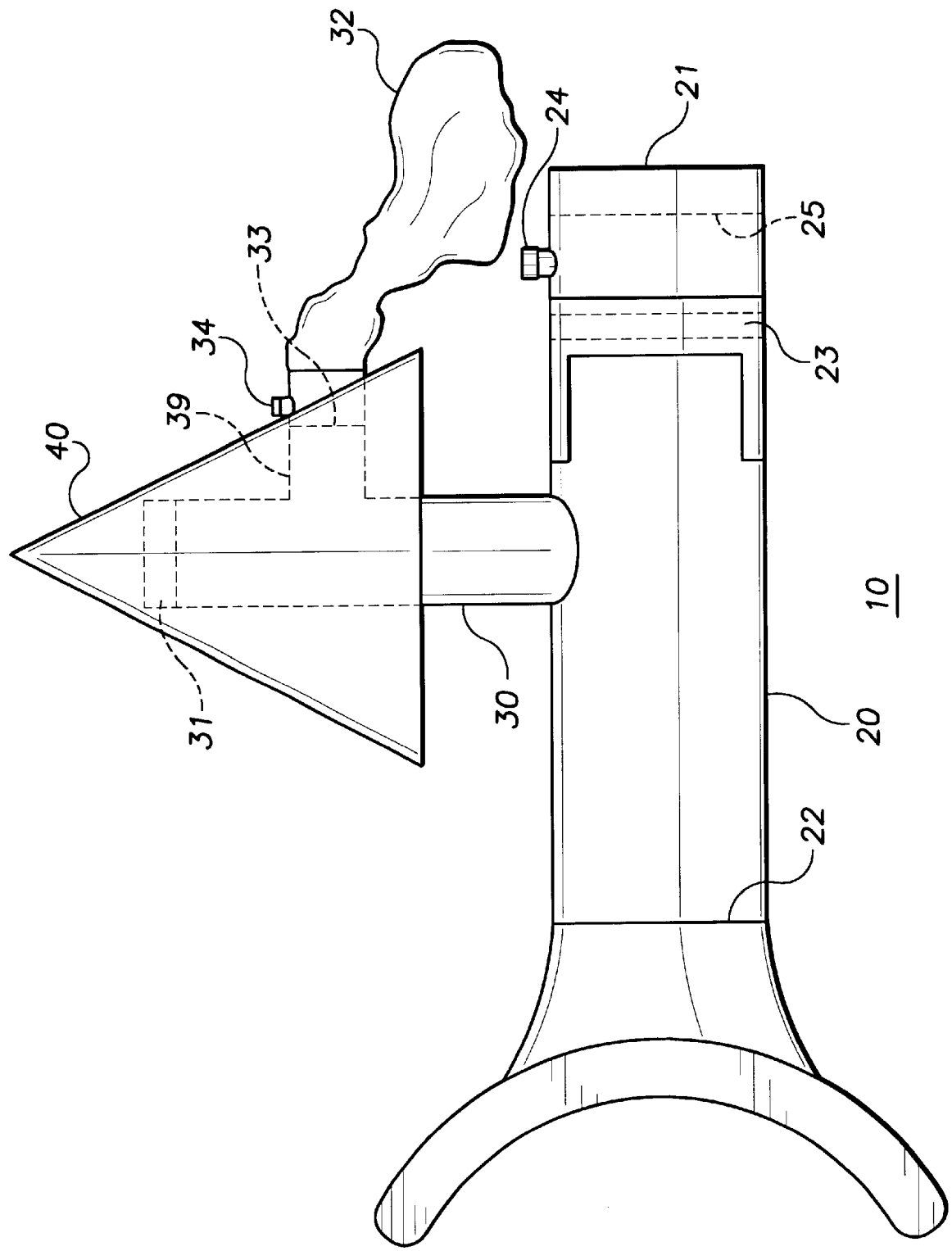

Children are often intimidated and frightened when placed in a medical setting as a patient. They are sick and do not feel well from the very start. Then, they are brought to a strange place with other sick and nervous children and confronted with an unfamiliar authority figure (a doctor). As if that were not enough, the doctor may not have time, due to the nature of emergency medical treatment, to gently allay the fears of the children. With all of these factors, it is no wonder that children become nervous and scared; the apprehension is quite natural. Unfortunately, this apprehension can interfere with the medical treatment that these young patients need.

One particular problem faced by anesthetists daily is difficulty in the administration of anesthetic gas to children. Children often resist the use of conventional masks used to supply anesthetic gas to adults. They struggle to prevent doctors from covering their face with the mask, and they tense-up when the masks are in place, breathing in short, shallow breaths instead of deeply breathing the gas. This reduces the effectiveness of the anesthetic gas and makes the entire medical procedure more difficult.

The instant invention, referred to as a Pediatric Preparatory and Induction Anesthesia Device ("PPIAD"), was developed to reduce these problems inherent in using gas to induce anesthesia in children during medical procedures. It presents the mask as a non-threatening toy, incorporating familiar play-things in order to put the child at ease. This helps the doctors to be able to apply the mask with much less struggle.

By presenting itself as a toy, the PPIAD can also assist in the preparation of young children for the application of anesthetic gas in the operating room. The device can be given to the children while they are waiting for the medical procedure (without the anesthesia circuit being attached), allowing them to play with the "toy." This prepatory process allows the children to become familiar with the device, so that when it is used in the operating room (now attached to the anesthesia circuit), the children are not frightened. This prepatory work with the device in the waiting room also allows the children to learn how to use the device properly, since the desired type of breathing is required for the device's toy-like features to operate. Thus, the PPIAD simultaneously teaches the child how to use the device properly (aiding in the application of the anesthetic gas) while calming the child's fears regarding both the anesthesia and the medical procedure by eliminating some of the uncertainty and unfamiliarity before the child even enters the operating room.

The PPIAD also encourages the child to breathe deeply which greatly increases the effectiveness of the anesthetic gas. This is accomplished by incorporating a balloon, a whistle, or similar items into the device. In order for the child to play with the familiar, toy-like objects, the child must deeply inhale the gas. In this way, the PPIAD uses a game-like setting not only to make application of the mask much less frightening to children but also to actually encourage children to actively participate in such a way that they make the anesthetic gas function more effectively. The result is a much easier and more pleasant experience for all involved (the children are less frightened and receive more effective care, the parents do not have to see their children in such an apprehensive state, and the doctors do not have to struggle with their young patients and try to convince them to breathe properly) and better anesthetic gas delivery to children.

There are other devices which have been developed for delivering gases to children in a medical setting. Many pediatric devices try to disguise themselves as toys. One example is seen in U.S. Pat. No. 5,690,096. It uses a teddy bear-like device to blow oxygen across a child's face. While this device does use toy-like equipment to administer oxygen, such a blow-by device is not useful for administering anesthesia because it does not trap the gas. Releasing anesthetic gas into the atmosphere in a medical setting would be dangerous because the gas could affect the doctors and others tending to the child.

Another device is shown in U.S. Pat. No. 5,697,363. It is an anesthesia administering device designed to look like a helmet for a pilot. However, it administers gas through a nose-piece and does not cover the child's mouth. This means that a child can easily refuse to take in the gas by breathing through the mouth. In addition, it does not encourage the child to deeply inhale; it simply applies the gas while the child breathes in the standard manner. Thus, while the pediatric field often uses toy-like devices to put children at ease, there is no current device which facilitates the administration of anesthetic gas to children as efficiently as does the Pediatric Prepatory and Induction Anesthesia Device.

SUMMARY OF THE INVENTION

Generally, the present invention relates to a device for administering gas to a patient. While this invention is particularly well-suited for use as an anesthetic gas delivery system when treating children, it is in no sense limited to the pediatric field or to delivering anesthetic gas. The present invention has as an objective to administer anesthetic gas to patients. It seeks to do so in a non-threatening way, using familiar toy-like items to sooth the fears of the patient, particularly when the patient is a child. Another object of this invention is to encourage the patient to deeply inhale the gas. This is accomplished by incorporating toy-like items into the device which require moving gases to operate. Yet another objective is for the invention to capture the exhaled gas and to prevent the gas from entering the general atmosphere where it could affect others besides the patient. And still another objective is to prepare the patient for the application of the gas by teaching the patient how to properly breathe through the device (using various toy-like devices to signal proper breathing) so as to facilitate the induction of anesthesia. In accomplishing these objectives, the Pediatric Prepatory Induction Anesthesia Device helps doctors administer anesthetic gas more effectively.

Generally in the PPIAD, the gas flows from the anesthesia circuit into the device through a one-way valve. This allows the gas to enter the device while preventing gases exhaled from the patient from interfering with the entry gas flow. The gas then enters the main body of the PPIAD. This is a tube which leads to the breathing mask with a T-connection to another tube which functions as the exhaust outlet. Inside the main body tube is a whistle device which makes noise when the patient inhales or exhales deeply. This toy-like feature of the device encourages the patient to breathe the gas deeply. The gas passes through the main body tube (when the patient inhales) to the patient through a mask attachment which is wide enough to cover the patient's mouth and nose. Thus, when the patient inhales, the gas enters through the one-way valve at one end of the main body tube, passes through the main body tube and past the T-connection (due to the lower pressure vacuum force created when the patient inhales), and enters the patient through the mask attachment. When the patient exhales, the exhaust passes through the mask attachment and into the main body tube. There, it exits through the T- connection into the exhaust tube since the one-way valve at the other end of the main body tube prevents the exhaust from escaping elsewhere. The exhaust tube leads to another one-way valve which allows the exhaust to exit the exhaust tube but does not allow the exhaust to seep back into the exhaust tube. On the other side of the one-way valve in the exhaust tube is a receptacle for capturing the exhaust gases. Typically, this receptacle is an inflatable container similar to a balloon which expands as the patient exhales more deeply. This encourages the patient to breathe the gases in more deeply as they attempt to exhale with enough force to inflate the receptacle, and speeds the anesthetic process. Thus, the PPIAD encourages the patient to deeply inhale (to activate the toy-like features of the device) and captures the exhaled gases so that the medical gases do not affect others. These and other objects of the PPIAD will be more apparent to those skilled in the art from the following detailed description of the invention.

BRIEF DESCRIPTION OF THE INVENTION

Reference will be made to the drawing where like parts are designated by the like numerals and wherein FIG. 1 is a schematic of a Pediatric Prepatory Induction Anesthesia Device.

DETAILED DESCRIPTION OF THE INVENTION

Referring now to the drawing in more detail, the preferred embodiment of the Pediatric Prepatory Induction Anesthesia Device is shown in FIG. 1, and is generally designated by the numeral 10. The PPIAD is comprised of a main body tube 20 and an exhaust tube 30. The main body tube 20 is a hollow, cylindrical tube. The exhaust tube 30 is also hollow. At one end of the main body tube 20 is located the anesthesia circuit connection 21. This is where the PPIAD 10 device will connect to the anesthesia circuit, allowing anesthetic gas to enter the PPIAD 10 through the anesthesia circuit connection 21. At the other end of the main body tube 20 is located the breathing mask connection 22. This is where the breathing mask which fits over the patient's face will connect to the PPIAD device. Somewhere along the length of the main body tube 20, and generally near the middle of the main body tube 20, the exhaust tube 30 rigidly connects to the main body tube 20 such that the exhaust tube 30 branches off of the main body tube 20. Thus, there is an opening linking the exhaust tube 30 to the main body tube 20 at the point where they connect so that they form a complete, hollow unit. removable main body one-way valve 25 is located within the main body tube 20. This main body one-way valve 25 is located between the anesthesia circuit connection 21 and the point of connection from which the exhaust tube 30 branches off of the main body tube 20. This main body one-way valve 25 allows gases to pass through it in the direction moving from the anesthesia circuit connection 21 towards the breathing mask connection 22, but it does not allow gases to flow through it the opposite direction, from the breathing mask connection 22 towards the anesthesia circuit connection 21. Thus, when in place, the main body one-way valve 25 prevents exhaust gases exhaled by the patient from flowing back into the anesthesia circuit and forces the exhaled gases to instead flow into the exhaust tube 30. The main body one-way valve 25 is removable, however, since some doctors may wish to have the exhaled gases pass into the anesthesia circuit for monitoring. When the main body one-way valve 25 is removed, the exhaust gases exhaled by the patient will flow back into the anesthesia circuit through the anesthesia circuit connection 21, with most of the exhaust gases bypassing the exhaust tube 30. The preferred method of operation for the PPIAD leaves the removable main body one-way valve 25 in place.

One or more sample line connections 24 are located on either the main body tube 20 and/or the exhaust tube 30. The sample line connection 24 is a small opening in the surface of either the main body tube 20 or the exhaust tube 30 from which a sample of the gas located within either the main body tube 20 or the exhaust tube 30 can be withdrawn. When the sample line connection 24 is not in use, it is closed so that the gases cannot escape. If the sample line connection 24 is in the main body tube 20, then it will generally be located on the end of the main body tube 20 away from the breathing mask connection 22, but the sample line connection 24 cannot be located between the main body one-way valve 25 and the anesthesia circuit connection 21 since that would not provide an effective sample. A noise-making device 23 is located within either the main body tube 20 or the exhaust tube 30. This noise-making device 23 is activated when moving gases contact it, so that it makes noise when the patient inhales or exhales. In the preferred embodiment, this noise-making device 23 is located within the main body tube 20 so that it is primarily activated when the patient inhales. Thus, it encourages the patient to inhale deeply, making a noise. If the noise-making device 23 is located in the exhaust tube 30, then it is primarily activated when the patient exhales.

The exhaust tube 30 may be either a hollow, cylindrical tube, or a hollow, cylindrical tube with a side-branch connection 39. If the exhaust tube 30 is simply a hollow, cylindrical tube, then located within the exhaust tube is an exhaust one-way valve 33. This exhaust one-way valve 33 allows gases to flow from the connection; to the main body tube 20 towards the end of the exhaust tube 30, but it does not allow gases to flow from the end of the exhaust tube 30 back towards the main body tube 20. On the side of the exhaust one-way valve 33 away from the main body tube 20 (towards the open end of the exhaust tube 30), the exhaust tube 30 connects to a gas collection unit 32. Generally, this gas collection unit 32 will inflate like a balloon when the patient exhales in order to encourage the patient to breathe deeply. Located between the exhaust one-way valve 33 and the gas collection unit 32 is a release outlet 34. When the release outlet 34 is closed, the gases exhaled by the patient must enter the gas collection unit 32 to be stored. When the release outlet 34 is opened, however, it allows the gases collected within the gas collection unit 32 to be drained so that the gas collection unit 32 can be emptied.

FIG. 1 shows the preferred embodiment of the PPIAD device, however, in which the exhaust tube 30 is a hollow, cylindrical tube with a side branch connection 39. When the exhaust tube 30 is so configured, the end of the exhaust tube 30 away from the connection to the main body tube 20 is plugged by a cap 31. This cap prevents gases from escaping through the far end of the exhaust tube 30. Within the side branch connection 39 is located the exhaust one-way valve 33. This exhaust one-way valve 33 allows gases to flow from the exhaust tube 30 towards the open end of the side branch connection 39, but it prevents gases from flowing the opposite direction. At the end of the side branch connection 39 farthest away from the main part of the exhaust tube 30, the side branch connection 39 is connected to the gas collection unit 32. Generally, this gas collection unit 32 will inflate like a balloon when the patient exhales in order to encourage the patient to breathe deeply. Located between the exhaust one-way valve 33 and the gas collection unit 32 is a release outlet 34. When the release outlet 34 is closed, the gases exhaled by the patient must enter the gas collection unit 32 to be stored. When the release outlet 34 is opened, however, it allows the gases collected within the gas collection unit 32 to be drained so that the gas collection unit 32 can be emptied.

In either configuration, the PPIAD is made less threatening in appearance by a cover 40, which conceals the device and is often designed to appear toy-like. The reason that the preferred embodiment uses an exhaust tube 30 which is a hollow cylinder with a side branch connection 39 is that this facilitates the use of the capped end of the exhaust tube 30 as a structural point on which the cover 40 may rest.

Thus, when the PPIAD device is configured as in the preferred embodiment in FIG. 1, it acts to improve anesthesia administration to children. When the patient inhales, the gas from the anesthesia circuit passes through the anesthesia circuit connection 21, through the main body one-way valve 25 (if it is left installed), through the noise-making device 23 (which should be activated when the patient is breathing as desired), through the main body tube 20 and past the exhaust tube 30 (due to the suction formed by the patient's inhaling), through the breathing mask connection 22, and into the patient's lungs. When the patient exhales (assuming that the main body one-way valve 25 is left installed), the exhaust gases will pass through the breathing mask connection 22, into the main body tube 20, and into the exhaust tube 30. They will be forced into the exhaust tube because of the main body one-way valve 25. Once in the exhaust tube 30, the exhaust gases will flow into the side branch connection 39 (since the cap 31 prevents the gases from escaping elsewhere), through the exhaust one-way valve 33, and into the gas collection unit 32. Generally, the exhaust gases will cause the gas collection unit 32 to inflate like a balloon, encouraging the patient to exhale deeply to blow it up. The exhaust gases will remain contained within the gas collection unit 32 (since the exhaust one-way valve 33 prevents their escape) until drained through the release outlet 34. The gas concentration and exhaust concentration can be monitored using the sample line connection 24 throughout the process. The cover 40 serves to comfort and relax the patient, giving the PPIAD the look of a toy.

The PPIAD operates differently if the main body one-way valve 25 is removed. When the patient inhales, the PPIAD acts in substantially the same way, with the gas from the anesthesia circuit passing through the anesthesia circuit connection 21, through the noise-making device 23, through the main body tube 20 and past the exhaust tube 30, through the breathing mask connection 22, and into the patient's lungs. However, when the patient exhales, the majority of the exhaust gases will pass through the breathing mask connection 22, through the main body tube 20, past the noise-making device 23, and through the anesthesia circuit connection 21 back into the anesthesia circuit, bypassing the exhaust tube 30. This optional use of the PPIAD provides doctors with flexibility in the monitoring of the patient's exhaust gases.

What I claim is:

1. A pediatric prepatory induction anesthesia device comprising:

a main body tube and an exhaust tube, said exhaust tube attached to said main body tube so that said exhaust tube branches from said main body tube at approximately a right angle, wherein said main body tube is further comprised of an anesthesia circuit connection at one end of said main body tube and a breathing mask connection at the other end of said main body tube and wherein said exhaust tube is further comprised of a side branch connection which branches from said exhaust tube;

a first, removable one-way valve within said main body tube located between the point on said main body tube where said exhaust tube branches off and said anesthesia circuit connection on said main body tube whereby gas is allowed to flow through said removable one-way valve from said anesthesia circuit connection towards said breathing mask connection but is not allowed to flow through said removable one-way valve from said breathing mask connection towards said anesthesia circuit connection;

a noise-making device, which is activated by contact with moving gas, located within either said main body tube or within said exhaust tube;

one or more sample line connections located on either said main body tube and/or said exhaust tube;

a gas collection unit connected to said side branch connection of said exhaust tube whereby gas passing through said exhaust tube can enter said gas collection unit;

a cap for said exhaust tube, wherein said cap plugs the open end of said exhaust tube and thereby forces gas passing into said exhaust tube to enter said gas collection unit;

a second one-way valve located in said side branch connection on said exhaust tube whereby gas is allowed to flow through said second one-way valve into said gas collection unit, but is not allowed to flow through said second one-way valve out of said gas collection unit; and a gas release outlet located adjacent to said second one-way valve wherein said gas release outlet is on the side of said second one-way valve closest to said gas collection unit.

2. A pediatric prepatory induction anesthesia device as in claim 1 further comprising a cover for the device.

3. A pediatric prepatory induction anesthesia device as in claim 2 wherein said gas collection device is an inflatable container.

4. A pediatric prepatory induction anesthesia device as in claim 1 wherein said gas collection unit is an inflatable container.

5. A pediatric prepatory induction anesthesia device as in claim 4 wherein said side branch connection on said exhaust tube branches out from said exhaust tube at approximately a right angle.

* * * * *